(12) United States Patent
Maiorino et al.

(10) Patent No.: US 9,572,559 B2
(45) Date of Patent: Feb. 21, 2017

(54) PORT SITE CLOSURE

(71) Applicant: Covidien LP, Mansfield, MA (US)

(72) Inventors: Nicholas Maiorino, Branford, CT (US);
Saumya Banerjee, Hamden, CT (US);
Timothy Sargeant, Guliford, CT (US);
Arpan Desai, Hamden, CT (US)

(73) Assignee: Covidien LP, Mansfirld, MA (US)

( * ) Notice: Subject to any disclaimer, the term of this patent is extended or adjusted under 35 U.S.C. 154(b) by 297 days.

(21) Appl. No.: 14/197,670

(22) Filed: Mar. 5, 2014

(65) Prior Publication Data
US 2014/0276998 A1 Sep. 18, 2014

Related U.S. Application Data

(60) Provisional application No. 61/789,359, filed on Mar. 15, 2013.

(51) Int. Cl.
A61B 17/08 (2006.01)
A61B 17/00 (2006.01)

(52) U.S. Cl.
CPC .. *A61B 17/0057* (2013.01); *A61B 2017/00637* (2013.01); *A61B 2017/00659* (2013.01); *A61B 2017/00951* (2013.01)

(58) Field of Classification Search
CPC ............... A61B 17/0057; A61B 2017/00637; A61B 2017/00659; A61B 2017/00951
See application file for complete search history.

(56) References Cited

U.S. PATENT DOCUMENTS

| 3,874,388 | A | 4/1975 | King et al. |
| 5,540,711 | A | 7/1996 | Echeverry et al. |
| 5,769,864 | A | 6/1998 | Kugel |
| 6,391,060 | B1 | 5/2002 | Ory et al. |
| 6,596,002 | B2 | 7/2003 | Therin et al. |
| 7,179,272 | B2 | 2/2007 | Kieturakis et al. |
| 7,704,268 | B2 | 4/2010 | Chanduszko |
| 7,785,334 | B2 | 8/2010 | Ford et al. |
| 2004/0220592 | A1 | 11/2004 | Mueller et al. |
| 2005/0283187 | A1 | 12/2005 | Longson |
| 2006/0015142 | A1 | 1/2006 | Malazgirt |
| 2007/0083229 | A1 | 4/2007 | Deutsch |

(Continued)

FOREIGN PATENT DOCUMENTS

| EP | 0534696 A1 | 3/1993 |
| EP | 2308380 A1 | 4/2011 |

OTHER PUBLICATIONS

European Search Report dated Feb. 23, 2015 issued in European Application No. 14159734.

(Continued)

*Primary Examiner* — Ashley Fishback

(57) ABSTRACT

A closure device for port site closure is provided. The closure device includes an end effector having a top surface and a bottom surface. A stem extends upwardly from a midsection of the top surface of the end effector. The stem has a free end, a distal end, and a middle portion therebetween. An attachment member extends from the distal end of the stem and is fixedly attached to the top surface of the end effector. The attachment member has a width smaller than a width of the distal end. At least one notch is defined by a gap between the distal end of the stem and the top surface of the end effector.

20 Claims, 4 Drawing Sheets

(56) References Cited

U.S. PATENT DOCUMENTS

| | | |
|---|---|---|
| 2007/0198059 A1 | 8/2007 | Patel et al. |
| 2008/0071310 A1 | 3/2008 | Hoffman et al. |
| 2008/0161847 A1 | 7/2008 | Sandhu et al. |
| 2009/0004239 A1 | 1/2009 | Ladet et al. |
| 2009/0143815 A1 | 6/2009 | Eidenschink et al. |
| 2011/0087271 A1* | 4/2011 | Sargeant ............ A61B 17/0057 606/213 |
| 2011/0087272 A1 | 4/2011 | Sargeant et al. |
| 2011/0196420 A1 | 8/2011 | Ebner |
| 2011/0224728 A1 | 9/2011 | Martin et al. |
| 2011/0301619 A1 | 12/2011 | Walters |
| 2012/0116447 A1 | 5/2012 | Stanley et al. |
| 2012/0316594 A1 | 12/2012 | Palese |
| 2014/0207183 A1* | 7/2014 | Shipp ................ A61B 17/0057 606/213 |

OTHER PUBLICATIONS

European Search Report dated Jun. 30, 3015, issued in European Application No. 14159734.

* cited by examiner

PORT SITE CLOSURE

CROSS-REFERENCE TO RELATED APPLICATIONS

This application claims the benefit of and priority to U.S. Provisional Patent Application No. 61/789,359, filed Mar. 15, 2013, the entire disclosure of which is incorporated by reference herein.

BACKGROUND

1. Technical Field

The present disclosure relates to a system and method for closing a port site. More particularly, the present disclosure provides a closure device inserted into an introducer such that an end effector of the closure device is positioned over a peritoneum within an abdominal wall. The introducer is removed and the closure device remains in position.

2. Background of Related Art

Laparoscopy, which is only one example of minimally invasive surgery (MIS), is a modern surgical technique in which operations in the abdomen are performed through small incisions as compared to larger incisions needed in traditional surgical procedures. Laparoscopy provides a number of advantages versus open procedures that include reduced pain from infection and hemorrhaging and shorter recovery time. The abdomen is usually insufflated, or essentially blown up like a balloon, with carbon dioxide gas ($CO_2$). This elevates the abdominal wall above the internal organs like a dome to create a working and viewing space. $CO_2$ is used because it is common to the human body and can be absorbed by tissue and removed by the respiratory system. It is also non-flammable, which is important because electrosurgical devices are commonly used in laparoscopic procedures.

During typical laparoscopic surgeries to close the muscle fascia layer and the skin layer at the port site, the surgeon typically closes these layers at the port site with sutures. After a typical laparoscopic surgery, the surgeon typically closes the muscle fascia layer and the skin layer at the port site with sutures. However, closing port sites with sutures can be time consuming, tedious, and difficult. Obese and morbidly obese patients can have several to many inches of abdominal wall, making closure of the muscle and skin layers quite difficult. Additionally, there is an increased risk of damaging organs and/or the bowel of the patient with a needle due to limited visibility.

The present disclosure provides a system and method for eliminating the need for suturing the muscle fascia and skin layers and thus a reduced risk for damaging organs and/or the bowel of the patient. Additionally, the present system provides an increased ease of use and reduces closure time required.

SUMMARY

In an embodiment of the present disclosure, a closure device for port site closure is provided. The closure device includes an end effector having a top surface and a bottom surface. A stem extends upwardly from a midsection of the top surface of the end effector. The stem has a free end, a distal end, and a middle portion therebetween. An attachment member extends from the distal end of the stem and is fixedly attached to the top surface of the end effector. The attachment member has a width smaller than a width of the distal end. At least one notch is defined by a gap between the distal end of the stem and the top surface of the end effector. The middle portion of the stem has a first edge and a second edge. Preferably, each of the first and second edges having a plurality of serrations therealong. In one embodiment, the stem and the end effector of the closure device are made from a porous, biodegradable mesh.

In an alternate embodiment, the end effector is multi-layered and may have an adhesive configured to secure the end effector to a peritoneum.

According to another embodiment, the end effector is circular and may have a plurality of slits extending from a perimeter of the end effector towards a mid point.

In yet another alternate embodiment, the end effector is symmetrical with a first rim, a second rim, and midsection therebetween. The first and second rims are equal in width and the midsection has a width smaller than both the first and second rims.

In still another alternate embodiment, a method for port site closure along an abdominal wall is provided. The method includes the steps of providing an introducer. The introducer includes a semi-circular hollow tube having a first surface and a second portion. The first surface is concave towards the second portion. A closure device is also provided. The closure device includes an end effector having a top surface and a bottom surface. A stem extends upwardly from a midsection of the top surface of the end effector. The stem has a free end, a distal end, and a middle portion therebetween. An attachment member extends from the distal end of the stem and is fixedly attached to the top surface of the end effector. The attachment member has a width smaller than a width of the distal end. At least one notch is defined by a gap between the distal end of the stem and the top surface of the end effector. The method further includes accessing a peritoneum within an abdominal cavity of a patient through a cannula and inserting the introducer through the cannula. Next, the surgeon pushes the end effector and stem through the introducer such that the end effector is released within the abdominal cavity and the stem remains within the introducer. The cannula and introducer are removed from the abdominal wall thereby allowing the top surface of the end effector to rest adjacent the peritoneum. Finally, the stem of the closure device is cut just below the skin level and the skin is closed using sutures, adhesives, bandages, or other techniques as are known in the art.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Figure 1:
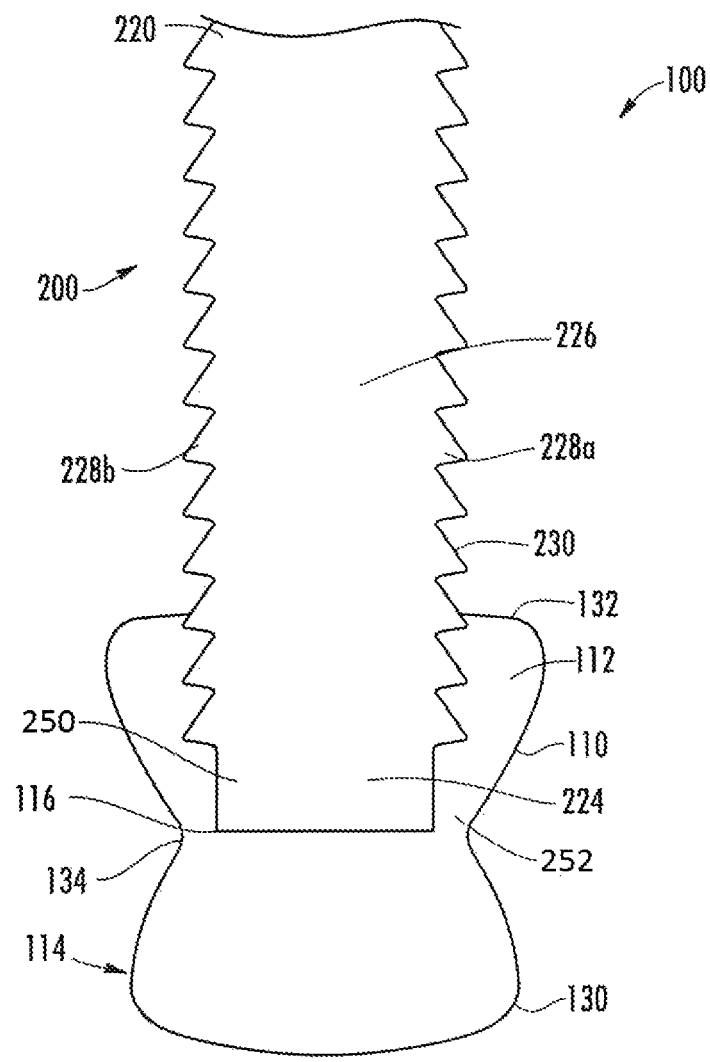
FIG. 1 is a front view an embodiment of a closure device with an end effector according to the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail. Although the present disclosure is discussed in terms of a minimally invasive laparoscopic procedure, the presently disclosed instrument is usable in other minimally invasive procedures.

FIG. 1 illustrates an embodiment of the closure device of the present invention. The closure device 100 includes an end effector 110 having a top surface 112 and a bottom surface 114. A stem 200 extends upwardly from a midsection 116 of the top surface 112 of the end effector 100. The stem 200 includes a free end 220, a distal end 224, and a middle portion 226 therebetween. The middle portion 226 includes a first edge 228a and a second edge 228b. A plurality of serrations 230 are positioned along each of the first edge 228a and second edge 228b. Preferably, the serrations 230 resemble uniform cut-outs or gaps along the first and second edges 228a, 228b. The serrations 230 frictionally engage the tissue of an abdominal cavity and allow the stem 200 to remain in position during the surgical procedure. In an alternate embodiment, the stem 200 may include a plurality of rectangular portions held together such that gaps are formed between each portions. Various additional embodiments of the design of the serrations 230 are contemplated.

The stem 200 is fixedly attached to the top surface 112 of the end effector by a connector 250. The connector 250 extends from the distal end 224 of the stem 200. The connector 250 has a width smaller than a width of the distal end 224, such that at least one notch 252 is defined by a gap between the distal end 224 of the stem 200 and the top surface 112 of the end effector 100. The notch 252 allows the peritoneum to resiliently close beyond the edges of the stem 200 and contour around the connector 250, thereby maintaining the end effector 100 in position. In an alternate embodiment, the top surface 112 may also include an adhesive to affix the end effector to the peritoneum of the abdominal wall.

Figures 2, 3:
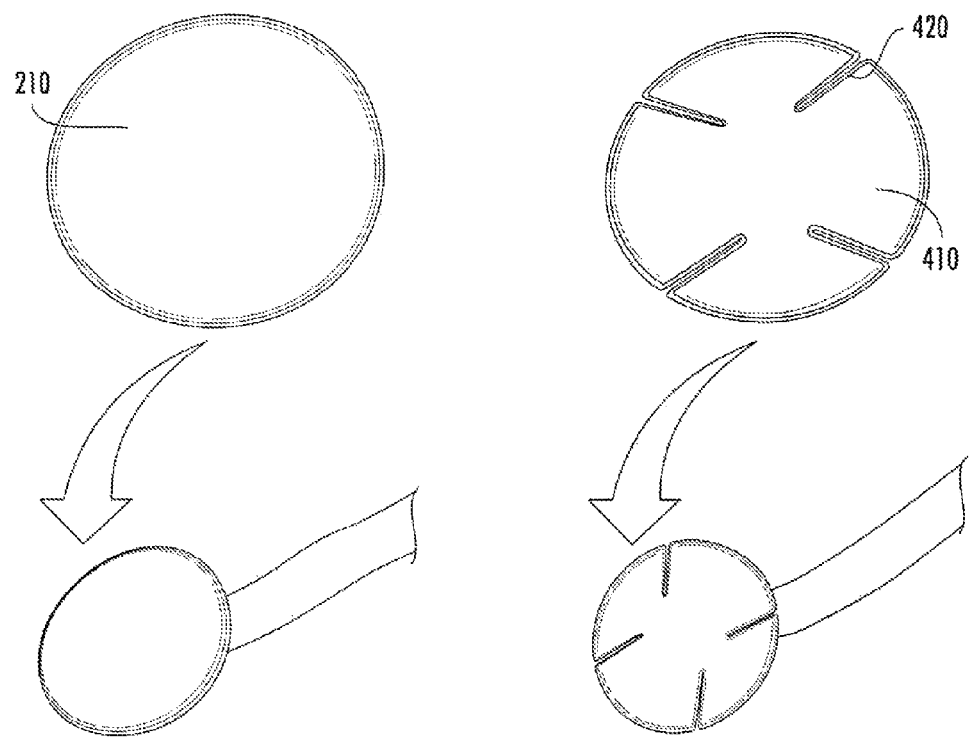
FIGS. 2 and 3 are alternate embodiments of an end effector of the closure device of FIG. 1.

The end effector 110 may be of varying shapes and sizes to fit the needs of the surgical procedure. As shown in FIG. 1, the end effector 110 is symmetrical having a first rim 130, a second rim 132, and a midsection 134 therebetween. The first and second rims being equal in width and the midsection having a width smaller than the first and second rims. However, as shown in FIGS. 2 and 3, end effector can have alternative forms. In FIG. 2, the end effector 210 is shown as circular. In FIG. 3, the end effector 410 is circular having a plurality of slits 420 extending from a perimeter of the end effector 410 towards a midpoint. Slits 420 and varying the shape of the end effector 110, 210, 410 facilitate insertion of the respective closure device into a deployment device. Further, by altering the shape of the end effector, there is reduced interaction between the end effector and inner surfaces of the deployment device, which reduces frictional engagement therebetween and reduces the potential for the closure device to bind within the deployment device.

In the preferred embodiment, the closure device 100 is made from a porous substrate. Porous substrates in accordance with the present disclosure may be a mesh, fibrous sheet, patch, foam, film, or composite thereof. The term "porous" as used herein may define openings and spacings which are present as a surface characteristic or a bulk material property, partially or completely penetrating the substrate. Suitable materials for forming a porous substrate include, but are not limited, to fibrous structures (e.g., knitted structures, woven structures, non-woven structures, etc.), foams (e.g., open or closed cell foams), and perforated films. Use of a porous substrate may allow for quicker healing through the openings formed therein.

The porous substrate should have the following characteristics: sufficient tensile strength to support a fascial wall during repair of a defect in the fascial wall causing a hernia; sufficiently inert to avoid foreign body reactions when retained in the body for long periods of time; easily sterilized to prevent the introduction of infection when the substrate is implanted in the body; and suitably easy handling characteristics for placement in the desired location in the body. The porous substrate should be sufficiently pliable to conform to a fascial wall and flex with movement of the wall, while being sufficiently rigid to retain its shape. The porous substrate should also be sufficiently strong to avoid tearing of portions thereof.

The porous substrate may be fabricated from any biodegradable polymer that can be used in surgical procedures. The term "biodegradable" as used herein is defined to include both bioabsorbable and bioresorbable materials. By biodegradable, it is meant that the materials decompose or lose structural integrity within a clinically relevant time period, under body conditions (e.g., enzymatic degradation or hydrolysis), or are broken down (physically or chemically) under physiologic conditions in the body such that the degradation products are excretable or absorbable by the body. In embodiments, biodegradable compositions of the present disclosure may degrade over a period of time from about 1 week to about 6 months, in embodiments from about 2 weeks to about 4 months, in embodiments from about 6 weeks to about 3 months. It should be understood that such materials include natural, synthetic, bioabsorbable, and/or certain non-absorbable materials, as well as combinations thereof.

The porous substrate may be used to deliver therapeutic agents into the tissue. In general, therapeutic agents may be incorporated into the porous substrate during manufacture or formation of the porous substrate, such as by free solution, suspension, liposomal delivery, microspheres, etc., or by coating a surface of the porous substrate, or selective regions thereof, such as by polymer coating, dry coating, freeze drying, or applying the coating directly to the porous substrate surface. In embodiments, at least one therapeutic agent may be combined with a component of an absorbable porous substrate to provide release of the therapeutic agent via degradation of the surgical implant.

Figure 4:
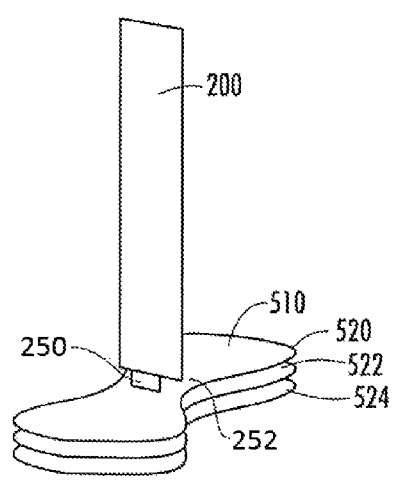
FIG. 4 is a perspective view of the closure device of FIG. 1 according to an embodiment of the present disclosure.

Turning now to FIG. 4, an alternate embodiment of the end effector 510 is shown made of multiple layers. As shown, the end effector 510 is comprised of three layers, a proximal layer 520, a middle layer 522, and a distal layer 524. The proximal layer 520 is disposed against the peritoneum when the end effector 510 is secured within the abdominal cavity. The proximal layer 520 is preferably soft with the ability to integrate into the abdominal wall. The middle layer 522 is stiffer than the proximal layer 520 and reinforces the end effector 510. The distal layer 524 is exposed within the abdominal cavity and therefore is preferably low profile and/or includes an anti-adhesion layer or anti-adhesion barrier. As shown, the proximal, middle, and distal layers 520, 522 and 524 are uniform in thickness, however, the thickness of each layer can vary depending the needs of area being treated.

Figure 5:
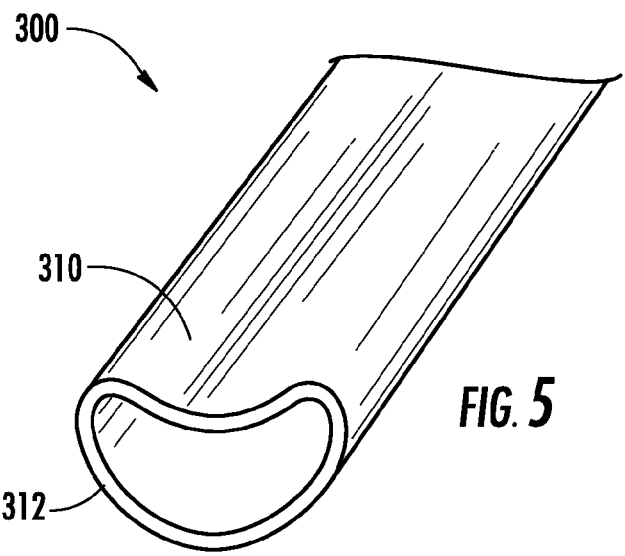
FIG. 5 is a perspective view of an introducer according to the present disclosure.
Figure 6:
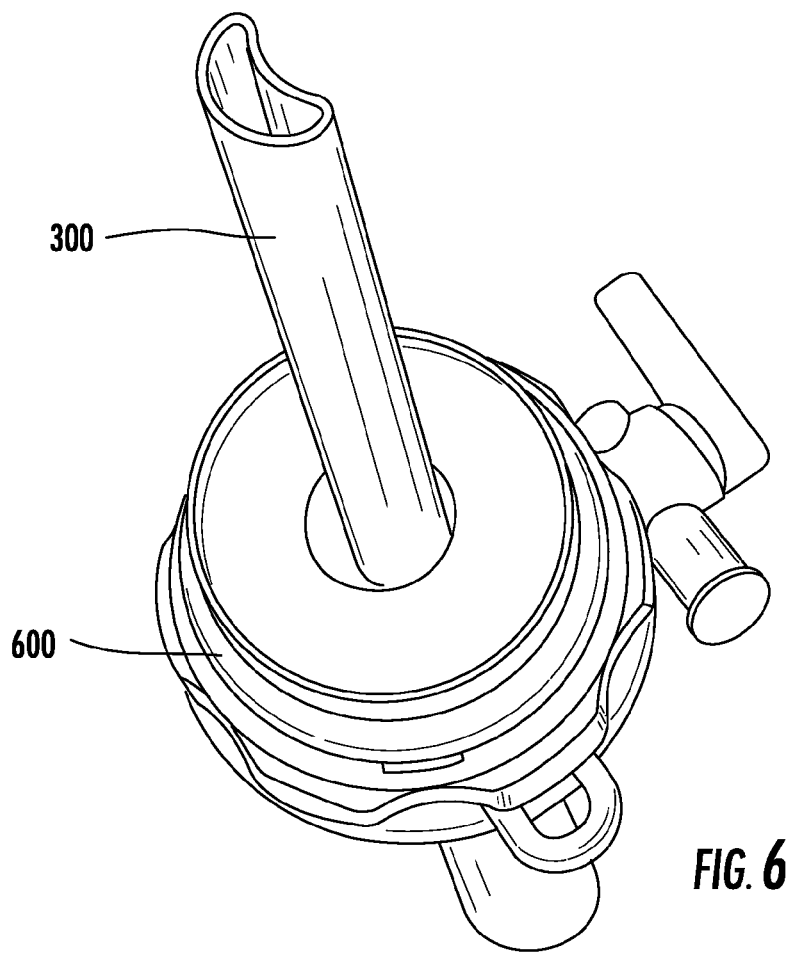
FIG. 6 is a perspective view of the introducer of FIG. 5 inserted through a cannula.

Generally, during laparoscopic surgeries, the surgeon inserts a trocar or cannula to access the abdominal cavity. The cannula allows the surgeon to insert surgical instruments, as needed, to treat the affected area. In the present application, the closure device 100 is pushed through an introducer 300 (shown in FIG. 5) which is inserted through the cannula 600 (shown in FIG. 6). The introducer 300 allows the closure device 100 to reach beyond the peritoneum and the removal of the introducer 300 exposes the end effector 110 into the abdominal cavity. The stem 200 extends through the peritoneum and the abdominal wall. The introducer 300 is a semi-circular hollow tube having a first surface 310 and a second portion 312. In one embodiment, the first surface 310 is concave towards the second portion 312. The concave feature of the first surface 310 prevents the stem 200 from falling through the introducer 300 as the closure device 100 is being advanced into the introducer 300. The friction from the serrations 230 of the stem 200 and the curve of the first surface 310 of the introducer 300 allow the surgeon to push the closure device 100 through the introducer 300 without the fear of losing the closure device 100 within the abdominal cavity. Additionally, the shape of the introducer 300 allows the introducer 300 to be inserted into standard cannulas known and used in the art. FIG. 6 illustrates a cannula 600 with the introducer 300 inserted therethrough, prior to insertion of the closure device 100. Using an introducer, such as introducer 300, having a curved or arcuate configuration allows the stem 200 of the closure device 100 to have a width that is wider than a width of the cannula 600. As an example, a closure device with a stem having a width of 12 mm would be readily insertable into, and through, a 10 mm cannula. The added width of the stem 200 helps engage the edges of the incision and facilitates maintaining the closure device 100 in place. Further still, the plurality of serrations along edges of the stem 200 assist in engaging the edges of the incision to help hold the closure device 100 in position.

Figure 7:
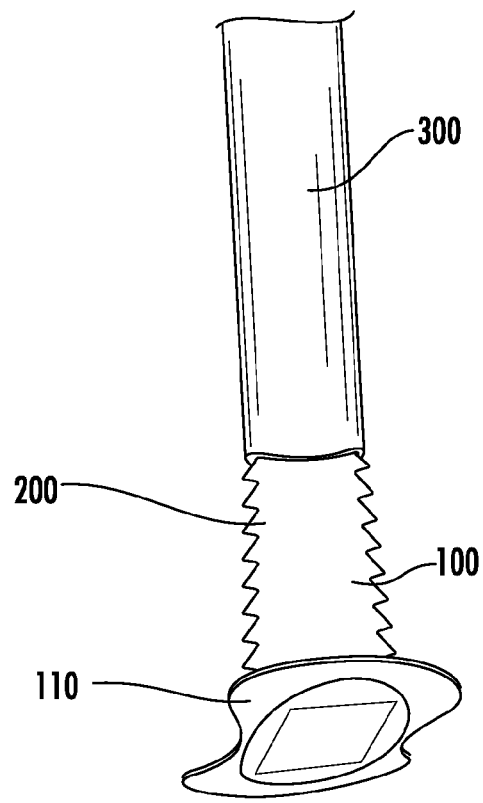
FIG. 7 is a side view of the introducer of FIG. 5 with the closure device of FIG. 1 positioned within.

FIG. 7 shows the closure device 100 advanced through the introducer. The closure device 100 is inserted and pushed through the introducer 300 at one end until the end effector 100 is released or pops out from the introducer 300 at the opposing end. The surgeon may push the closure device 100 through the introducer 300 as far as desired before removing the introducer and placing the end effector 110 against the peritoneum. It is contemplated that the closure device 100 is pre-loaded into the introducer 300 prior to use by the surgeon. It is also contemplated that several of the disclosed closure devices may be provided with the introducer 300 and the surgeon would load the closure device into the introducer 300 prior to performing the surgical procedure. Alternatively, several closure devices and several introducers may be provided as part of a kit.

Figure 8:
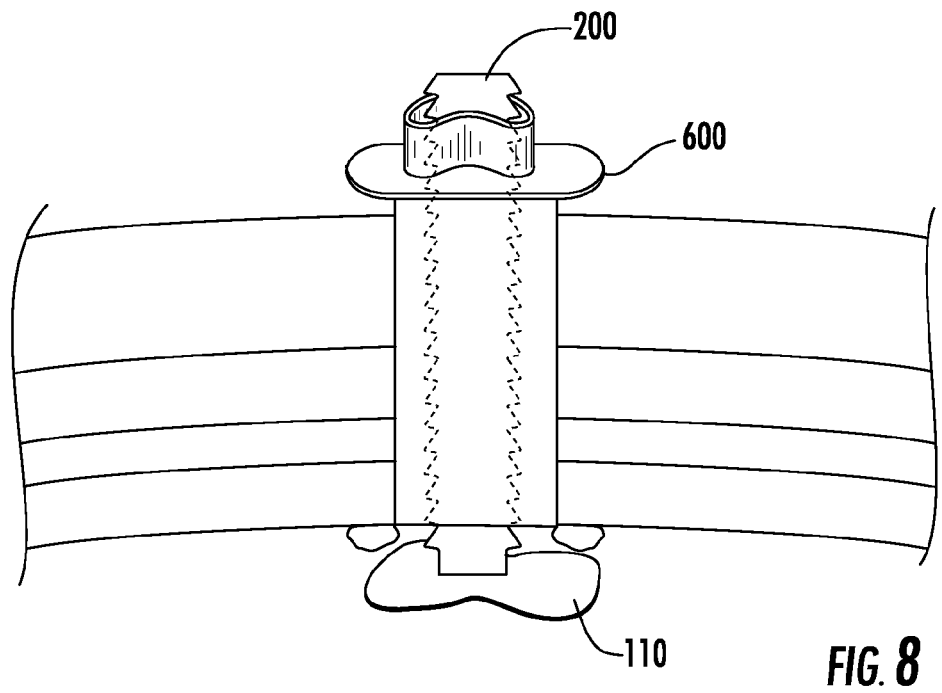
FIG. 8 is a side view of the closure device within the introducer and advanced within an abdominal cavity according to an embodiment of the present disclosure.

As shown in FIG. 8, a method for port site closure according to an embodiment of the present application will be described. First, an introducer 300 and a closure device 100, as described hereinabove, are provided. The end effector 110 of the closure device 100 may be of varying shapes or layers as required for the peritoneum and affected area being treated. Next, the surgeon accesses a working space through a cannula 400 where a distal end of the cannula is disposed beyond the peritoneum. The surgeon then inserts the introducer 300 through the cannula 400. The closure device 100 is then pushed through or expelled from the introducer 300 with the end effector 110 leading the stem 200 through the introducer 300. As the closure device 100 is pushed through the introducer 300, the end effector 110 is released with the abdominal cavity and a portion of the stem 200 remains within the introducer 300. The surgeon may adjust the stem 200 and the end effector 110 within the introducer 300 such that upon removal of the introducer 300, the end effector 110 is secured against the peritoneum along the abdominal wall. Next, the cannula 400 and introducer 300 are removed from the abdominal wall by an upward motion. As the introducer 300 is pulled upward, the stem 200 is pulled taught within the introducer 300 and the end effector 110 is also pulled upward by the motion of the stem 200 and the introducer 300. This upward motion places the end effector adjacent the peritoneum. As noted above, the notches 252 between the distal end 224 of the stem and the top surface 112 of the end effector help to secure the end effector 110 against the peritoneum by allowing the peritoneum to resiliently close beyond the edges of the stem 200 and around the connector 250 thereby maintaining the closure device 100 in position. The surgeon then cuts the stem 200 of the closure device 100 just below the skin layer and closes the skin by known methods (e.g., sutures, bandages, adhesives, etc.). The method described herein illustrates the use of the introducer through the cannula. However, it is contemplated the introducer can be used to access the peritoneum and abdominal cavity through known methods.

By employing any of the presently disclosed closure devices, herniation subsequent to the procedure is minimized. In comparing the presently disclosed closure device to a convention closure using sutures, the presently disclosed closure devices provide a comparable resistance to the separation of the incised tissues during a burst pressure test without the risks associated with suturing of tissue.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. A closure device for port site closure, the closure device comprising:
    an end effector having a top surface and a bottom surface;
    a stem extending upwardly from a midsection of the top surface of the end effector, the stem having a free end, a distal end and a middle portion therebetween, the stem having a first outer surface and a second outer surface opposite the first outer surface, the first and second outer surfaces extending from the distal end to the free end; and
    an attachment member extending from the distal end of the stem, the attachment member including a third outer surface and a fourth outer surface opposite the third outer surface, the third and fourth outer surfaces extending from the distal end of the stem, the attachment member fixedly attached to the top surface of the end effector and having a width smaller than a width of the distal end, such that at least one notch is defined by a gap between the distal end of the stem and the top surface of the end effector.

2. The closure device of claim 1, wherein the middle portion of the stem further comprises a first edge and a second edge, each of the first and second edges having a plurality of serrations therealong.

3. The closure device of claim 2, wherein the stem is made from a porous substrate.

4. The closure device of claim 1, wherein the end effector is multi-layered.

5. The closure device of claim 4, wherein the end effector includes an anti-adhesion layer and a porous layer, the porous layer adapted for contact with the peritoneum.

6. The closure device of claim 5, further including a layer of mesh disposed between the anti-adhesion layer and the porous layer.

7. The closure device of claim 1, wherein the end effector is circular.

8. The closure device of claim 7, wherein the end effector further comprises a plurality of slits extending from a perimeter of the end effector towards a mid point.

9. The closure device of claim 1, wherein the top surface of the end effector has an adhesive configured to secure the end effector to a peritoneum.

10. The closure device of claim 1, wherein the end effector is symmetrical having a first rim, a second rim and midsection therebetween, the first and second rims being equal in width and the midsection having a width smaller than both the first and second rims.

11. A closure device for port site closure, the closure device comprising:
  an end effector having a top surface and a bottom surface, the end effector being symmetrical having a first rim, a second rim and midsection therebetween, the first and second rims being equal in width and the midsection having a width smaller than both the first and second rims;
  a stem extending upwardly from a midpoint of the top surface of the end effector, the stem having a free end, a distal end and a middle portion therebetween, the stem defining a longitudinal axis and having first and second edges parallel to the longitudinal axis; and
  an attachment member extending from the distal end of the stem, the attachment member having first and second outer edges that extend between the stem and the end effector, the attachment member fixedly attached to the top surface of the end effector and having a width smaller than a width of the distal end, such that at least one notch is defined by a gap between the distal end of the stem and the top surface of the end effector.

12. The closure device of claim 11, wherein each of the first and second edges having a plurality of serrations therealong.

13. The closure device of claim 12, wherein the stem is made from a porous, biodegradable mesh.

14. The closure device of claim 11, wherein the end effector is made from a biodegradable mesh.

15. The closure device of claim 11, wherein the end effector is multi-layered.

16. The closure device of claim 11, wherein the top surface of the end effector has an adhesive configured to secure the end effector to a peritoneum.

17. A closure device for port site closure, the closure device comprising:
  an end effector having a top surface and a bottom surface, the end effector being circular having a plurality of slits extending from a perimeter of the end effector to a midpoint;
  a stem extending upwardly from a midpoint of the top surface of the end effector, the stem having a free end, a distal end and a middle portion therebetween, the stem having first and second outer surfaces that each extend from the free end to the distal end; and
  an attachment member extending from the distal end of the stem, the attachment member having first and second outer edges that extend between the stem and the end effector, the attachment member fixedly attached to the top surface of the end effector and having a width smaller than a width of the distal end, such that at least one notch is defined by a gap between the distal end of the stem and the top surface of the end effector.

18. The closure device of claim 17, wherein the middle portion of the stem further comprises a first edge and a second edge, each of the first and second edges having a plurality of serrations therealong.

19. The closure device of claim 18, wherein the stem is made from a porous, biodegradable mesh.

20. The closure device of claim 17, wherein the end effector is made from a biodegradable mesh.

* * * * *